United States Patent [19]

Konig et al.

[11] Patent Number: 5,648,565

[45] Date of Patent: Jul. 15, 1997

[54] PROCESS FOR THE ADIABATIC PREPARATION OF MONONITROTOLUENES

[75] Inventors: Bernd-Michael Konig, Düsseldorf; Helmut Judat, Langenfeld; Heinz Ulrich Blank, Odenthal-Glöbusch, all of Germany

[73] Assignee: Bayer Aktiengesellschaft, Leverkusen, Germany

[21] Appl. No.: 679,323

[22] Filed: Jul. 12, 1996

Related U.S. Application Data

[63] Continuation of Ser. No. 265,541, Jun. 24, 1994, abandoned, which is a continuation-in-part of Ser. No. 210,196, Mar. 17, 1994, abandoned.

[30] Foreign Application Priority Data

Feb. 14, 1994 [DE] Germany ............................ 44 04 614.6
Mar. 25, 1994 [DE] Germany ............................ 44 10 417.0

[51] Int. Cl.$^6$ ................................................... C07C 205/00
[52] U.S. Cl. ...................... 568/940; 568/924; 568/939; 568/927
[58] Field of Search .................... 568/927, 939, 568/924, 940

[56] References Cited

U.S. PATENT DOCUMENTS

| | | | |
|---|---|---|---|
| 2,256,999 | 9/1941 | Castner et al. . | |
| 4,021,498 | 5/1977 | Alexanderson et al. | 568/939 |
| 4,091,042 | 5/1978 | Alexanderson et al. | 568/939 |
| 4,112,006 | 9/1978 | Schubert et al. | 568/939 |
| 4,973,770 | 11/1990 | Evans | 568/927 |
| 5,313,009 | 5/1994 | Guenkel et al. | 568/927 |

FOREIGN PATENT DOCUMENTS 1297132  3/1992  Canada .

*Primary Examiner*—Shean C. Wu
*Attorney, Agent, or Firm*—Sprung Horn Kramer & Woods

[57] ABSTRACT

Mononitrotoluenes can be prepared by intensively mixing together toluene, nitric acid, sulphuric acid and water, simultaneously or successively in their total amount, and, in the case of continuous preparation, redispersing the mixture at least twice, for which purpose a mixing energy of 1 to 40 watts per liter of the total reaction mixture, preferably 3 to 30 W/l, is employed per volume of the reactor, and, for the continuous procedure, the back mixing is substantially repressed. Adiabatic reaction conditions are maintained.

20 Claims, No Drawings

PROCESS FOR THE ADIABATIC PREPARATION OF MONONITROTOLUENES

This application is a continuation of application Ser. No. 08/265,541, filed on Jun. 24, 1994 which is abandoned, which is a CIP of 08/210,196 filed on Mar. 17, 1994 which is abandoned.

BACKGROUND OF THE INVENTION

1. Field of the Invention

The present invention relates to a process for the highly selective preparation of mononitrotoluenes, which is free from waste acid and utilizes the heat of reaction.

Mononitrotoluenes are important intermediates for the production of plastics, dyes and auxiliaries.

2. Description of the Related Art

Mononitrotoluenes are prepared industrially by isothermic nitration of toluene at low temperatures (20° to 60° C.). Large amounts of highly contaminated waste acid arise in this, which must be disposed of or further processed expensively. A disadvantage of this process is that a considerable heat of reaction must be removed and this energy arises at a low temperature level so that it cannot be utilized.

A further disadvantage is that additional energy must be employed to concentrate the cold spent acid. Additionally, the separation of organic and inorganic phases after the nitration poses difficulties. Residual organic material must be removed from the spent acid by extraction with toluene. A known phenomenon in this is the black colouration of the spent acid ("black spend acid", U.S. Pat. No. 4,650,912), which leads to problems in the acid concentration.

In order to avoid the production of waste acid, processes must be sought which contain an integrated sulphuric acid concentration with utilization of the heat of reaction. This necessitates a circulating acid in which bi-products may not accumulate and high reaction temperatures in order to be able to concentrate the sulphuric acid industrially in an inexpensive manner.

For benzene, the adiabatic mononitration is described in a number of patents (U.S. Pat. Nos. 2,256,999, 4,021,498, 4,091,042, 4,973,770, EP 436443). The abovementioned energetic disadvantages in the isothermal toluene nitration do not apply to the adiabatic benzene nitration, since the heat of reaction thereof arises at a higher temperature level (temperature of the spent acid at the end of the reaction, for example >100° C.) and can be used to concentrate the acid. Although the extension of this proceeds the mononitration of toluene as mentioned in the abovementioned applications, it has never been described in an example. In contrast, the literature discloses that mononitrotoluenes are prepared isothermally at low temperatures (approximately 20°–60° C.) in order to avoid the intensified production and relatively high temperatures of dinitrotoluenes and oxidation products, such as nitrocresols and benzoic acids (Houben-Weyl, Volume X/1, p. 156, Thieme Verlag, Stuttgart 1971; Kirk-Othmer, Vol. 9, p. 395, Interscience, New York 1952). It is further known that the isothermal dinitration is carried out already in the temperature range of approximately 65°–85° C. It therefore had to be assumed that the adiabatic nitration of aromatic compounds other then benzene according to the above patents has a purely speculative character. In particular, the temperature quoted of 100° C. for the nitration of benzene in the example of U.S. Pat. No. 4,973,770 appeared not to be applicable to toluene.

In the process described in U.S. Pat. No. 4,973,770, attention is further focused on a single atomization and fine distribution of the benzene, by the aid of which the entire course of the reaction is to be controlled. In order to maintain the fine distribution for as long as possible, the coalescence of the atomized particles with each other and on the wall must be avoided. To avoid wall contact, a reactor having a large diameter relative to the nozzle diameter is used; as a result strong back-mixing is produced as in an ideally mixed stirred tank: according to exemplary embodiment of U.S. Pat. No. 4,973,770 in combination with FIG. 1, benzene is introduced into a reactor having a diameter of 75 mm through a spray nozzle having a diameter of 0.5 mm. With a total length of the reactor of 430 mm, the mixed acid is added at a distance of 150 mm from the nozzle, where the energy of the nozzle jet is already substantially consumed for the back-mixing. The mixing of the added mixed acid with the injected benzene therefore takes place at a lower energy level and with a lower intensity.

The claim of EP 436 443, according to which mixed acids containing nitronium ions are employed having molar compositions which are to be taken from FIG. 6 in EP 436 443 is also outside that which is familiar to those skilled in the art. Thus the point D emphasized in FIG. 6, in combination with p. 9, lines 10–12 of EP 436 443, indicates an acid of the composition 72.02 mol % $H_2SO_4$, 2.99 mol % $HNO_3$ and 24.99 mol % $H_2O$ which is equivalent to 91.71% by weight of $H_2SO_4$, 2.45% by weight of $HNO_3$ and 5.84% by weight of $H_2O$. Such a strong acid is not very suitable for the toluene nitration, in particular for the mononitration. Furthermore, circulation of the waste acid formed in this process is not industrially useful, since the necessary concentration to far above 90% by weight is too complex. This process is therefore not economically expedient and cannot provide those skilled in the art with information on achieving the present object.

SUMMARY OF THE INVENTION

As has surprisingly been found, toluene can be mononitrated adiabatically at relatively high reaction temperatures with high selectivity by the process according to the invention if the steps and conditions described below are employed.

The invention relates to a process for the continuous or discontinuous preparation of mononitrotoluenes by reaction of toluene with an $HNO_3/H_2SO_4/H_2O$ mixture with formation, essentially, of mononitrotoluenes and reaction water, characterized by the steps a) feeding the reaction participants toluene, $HNO_3$, $H_2SO_4$ and $H_2O$ in any sequence into a reactor equipped with mixing elements, in which a1) the amount of $HNO_3$ is 1–8% by weight, the amount of $H_2SO_4$ is 58–74% by weight and the amount of $H_2O$ is the remainder to 100% by weight and 100% by weight signifies the sum of $HNO_3+H_2SO_4+H_2O$, a2) the $H_2O$ is used as such, as dilution $H_2O$ of the $HNO_3$, as dilution $H_2O$ of the $H_2SO_4$ or in a plurality of the said forms and a3) the molar ratio of toluene to $HNO_3$ is 0.9–1.5, b) rapid and intensive mixing of the totality of the reaction participants, for which a mixing energy is employed of 1 to 40 watts per liter of the total reaction mixture, preferably 3 to 30 W/l, c) carrying out the reaction under adiabatic conditions, the reaction participants being fed in at temperatures such that the mixing proceeds in the range of 20°–110° C., preferably 30°–100° C., particularly preferably 40°-90° C., and the temperature at the end of the reaction does not exceed 135° C., d) separating the reaction mixture, after carrying out the reaction, into an organic and an inorganic phase and e) work-up of the substantially $HNO_3$- free inorganic phase by distillation with removal of water.

DETAILED DESCRIPTION OF THE INVENTION

The process according to the invention is carried out discontinuously or continuously, preferably continuously.

The continuous procedure can be carried out, for example, in the following manner: the reaction participants are rapidly mixed in totality in a mixing element and fed into a reactor as a mixture. The mixing time with the continuous procedure is generally less than 3 sec., for example 1 msec. to 2.99 sec., preferably 1 msec. to 2 sec. The reactor is insulated if required, substantially prevents back-mixing and is operated adiabatically. For the substantial prevention of back-mixing, the reactor is subdivided or is composed of a plurality of chambers or units; at the transfers between the reactor parts, the reaction mixture is redispersed. The mixture reacted to exhaustion runs off and is separated in a separation vessel; the separation proceeds rapidly. The organic phase is worked-up as is conventional, e.g. by washing and distillation, or is immediately fed to a second nitration. Generally, in particular when there is an excess of toluene, the inorganic phase separated off is virtually free of nitric acid. If this is not the case, in particular when there is an excess of nitric acid, residual nitric acid can be consumed in a post-reactor with addition of further toluene in the sense of a reactive extraction. The inorganic acid phase substantially free of nitric acid is preferably fed to a flash evaporation with utilization of the heat of reaction absorbed and under reduced pressure. In this case, water is removed from the acid and, preferably, simultaneously, the acid is brought to the feed concentration and the feed temperature. This acid is then, as $H_2SO_4$, directly suitable for use in step a). This return of the worked-up inorganic phase ($H_2SO_4$, $H_2O$) to the process results in a circulation technique for the $H_2SO_4$; it can be expedient to eject a small part of this $H_2SO_4$ to keep any contamination to a low level. In the event that the inorganic phase still contains toluene, nitrotoluene and any organic bi-products, it can be expedient to strip the inorganic phase before the flash evaporation to remove the organic compounds.

The water obtained subsequently as flash condensate is then of higher purity and its disposal is simpler. Obviously, the flash condensate can also be freed of organic compounds e.g. by stripping or phase separation, a residual flash condensate and a high-purity water-acid phase similarly remaining. The organic compounds arising in the post-reaction of the $HNO_3$ with further toluene and in the stripping or other separations, such as phase separation can be added to the process at a suitable position (toluene, (di)nitrotoluene) or are ejected and disposed of (impurities, by-products).

The reaction participants can be fed to the reactor equipped with mixing elements together, but also individually or as mixtures of two or three thereof simultaneously or successively. The feedstocks can be mixed, for example, in such a way that toluene and nitric acid or, if required, water are simultaneously or successively added as separate streams to the concentrated recycled sulphuric acid, in which case the nitric acid can be diluted by water and/or sulphuric acid and water. Toluene can also be premixed with water and sulphuric acid and the resulting emulsion is further intensively mixed with nitric acid which can be mixed with sulphuric acid and/or water. Furthermore, the toluene can also be intensively mixed with a mixed acid of sulphuric acid, nitric acid and water and then further treated according to the invention. Still other variants of the feeding of the reaction participants, their intensive mixing and further treatment are easily recognizable by those skilled in the art. For this purpose, mixing elements known in the prior art are suitable, e.g.: 1. static mixers, 2. pumps, 3. nozzles, 4. agitators or combinations thereof.

For the reaction to succeed, it is of little importance in which sequence and combination the reaction participants nitric acid and toluene as well as sulphuric acid and water are mixed together, as long as the reaction mixture has the composition according to the invention after the total mixing and the mixing takes place at the intensity according to the invention and, when the reaction is carried out continuously, substantially free from back-mixing.

The mixing intensity, in the case of the discontinuous procedure, apart from the high energy input, can also be characterized by the short reaction participant addition time which is 0.001 to 15%, preferably 0.001 to 3%, of the time which is required for the course of the reaction between toluene and nitric acid. It is thus also possible to carry out the process according to the invention batchwise in a stirred tank.

The feeding and intensive mixing of the reaction participants are followed, in the continuous procedure, by at least two redispersions. For this purpose, in the reactor there are present, preferably in sections, static mixer elements, if required also in the form of spherically shaped fixed internals, such as perforated metal sheets, slotted metal sheets, impingement baffles, veins or agitators or similar internals or elements known for this purpose to those skilled in the art.

Continuously operated reactors for the process according to the invention which can be mentioned by way of example are as follows: tubular reactors having internals for redispersion, such as veins, deflection baffles, static mixers or agitators and the like; intensively stirred tanks in a cascade arrangement; loop reactors having internals as above; combinations of a plurality of the said apparatuses; other reactors of equivalent action, such as chamber reactors with agitators in each chamber. Tubular reactors having internals are preferably used. The internals are preferably perforated metal sheets, if required spherically shaped. All internals represent subdivisions of the entire apparatus which equally serve for the redispersion and the substantial prevention of back-mixing.

After the intensive mixing, after each dispersion or after the mixture has flowed through a certain part-length of the reactor, coalescence of the dispersion droplets is observed which can be reversed by redispersion. The number of the redispersion operations is, according to the invention, 2 to 50, preferably 3 to 30, particularly preferably 4 to 20. To overcome the pressure drops occurring in this case, a mixing energy of 1 to 40 watts/liter, preferably 3 to 30 W/l, is added to the reaction system with the reaction participants, per liter of the total reaction mixture.

The reaction participants are mixed in the range from 20° to 110° C., preferably 30° to 100° C., particularly preferably 40 to 90° C. Adiabatic reaction conditions are maintained. The final temperature is dependent on the height of the mixing temperature, on the ratios of the amounts of the reaction participants and on the conversion rate; it generally does not exceed 135° C. and usually does not exceed 125° C.

The content of added nitric acid in the reaction mixture at the time of mixing is, based on the sum of nitric acid, sulphuric acid and water, 1 to 8% by weight, preferably 1 to 6% by weight, particularly preferably 1.5 to 4% by weight. Nitric acid can be used in highly concentrated form or in azeotropic form, but preferably in the form of the cheaply available "weak acid", having approximately 60–65% by weight.

The content of sulphuric acid in the reaction mixture at the time of mixing is, based on the sum of nitric acid, sulphuric acid and water, 58–74% by weight, preferably 60–72% by weight, particularly preferably 61–69% by weight. These figures do not include any process-specific impurities which may be contained in the event of an $H_2SO_4$ circulation technique.

The remainder to 100% by weight is $H_2O$. This can be used as such, as dilution $H_2O$ of the $H_2SO_4$, as dilution $H_2O$ of the $HNO_3$ or in a plurality of the said forms. $H_2O$ is preferably present as dilution $H_2O$ of both the $H_2SO_4$ and of the $HNO_3$.

Since the intensity of nitration with changing contents of nitric acid in the nitration acid is dependent on the ratio of sulphuric acid to water, it is determined and, if required, adjusted, on the basis of the sulphuric acid concentration, of the outflowing and substantially nitric acid-free spent acid. This $H_2SO_4$ concentration of the spent acid is to be according to the invention 62 to 74% by weight, preferably 64 to 72% by weight, particularly preferably 66 to 70% by weight. For reuse, the outflowing sulphuric acid is concentrated by 0.6–7 percentage points, in many cases by 1.5–3 percentage points, water (reaction water, possibly dilution water) being ejected by distillation. For this purpose the heat of reaction absorbed from the outflowing $H_2SO_4$ owing to the adiabatic reaction conditions is preferably utilized and reduced pressure in the range from 1 to 100 mbar, preferably 5–80 mbar, particularly preferably 10–75 mbar, is employed. This can be carried out, for example, in the form of a flash evaporation. The $H_2SO_4$ produced in this is suitable for use in step a). The ejection of water by distillation is preferably carried out in such a way that the temperature and concentration of the concentrated $H_2SO_4$ are directly equivalent to the values demanded in step a). Such a utilization of the heat of reaction makes the process according to the invention more economical than the known processes for the preparation of nitrotoluene.

Possible embodiments with respect to the mixed acids having varying compositions, outflowing $H_2SO_4$ concentrations, temperature conditions and pressure of the flash evaporation and degree of concentration of the $H_2SO_4$ may be summarized by way of example as follows (cases a, b and c):

| | a | b | c |
|---|---|---|---|
| Mixed acid | | | |
| $HNO_3$ (% by weight) | 4,00 | 3,00 | 2,50 |
| $H_2SO_4$ (% by weight) | 64,11 | 65,56 | 66,79 |
| $H_2O$ (% by weight) | 31,89 | 31,44 | 30,71 |
| Strength of the acids used | | | |
| $HNO_3$ (% by weight) | 60,0 | 60,0 | 60,0 |
| $H_2SO_4$ (% by weight) | 68,69 | 69,01 | 69,69 |
| Outflowing $H_2SO_4$ (% by weight) | 66,0 | 67,0 | 68,0 |
| Mixing temperature (°C.) | 80 | 85 | 90 |
| Final temperature (°C.), | 120 | 115 | 115 |

-continued

| | a | b | c |
|---|---|---|---|
| approximately Pressure in flash evaporation (approximate mbar) | 40 | 50 | 60 |

The molar ratio of toluene to $HNO_3$ is generally 0.9–1.5. In order to minimize the formation of undesirable dinitrotoluenes, the molar ratio of toluene to nitric acid is preferably 1.0 to 1.5, particularly preferably 1.03 to 1.3, very particularly preferably 1.05 to 1.2. However, if the nitrotoluenes available according to the invention are to be fed to the dinitration, broader molar ranges, e.g. 0.9–1.2 mol, preferably 0.9–1.05 mol, particularly preferably 0.95–1 mol, of toluene per mol of nitric acid are permissible.

The reaction of the process according to the invention proceeds according to the formula:

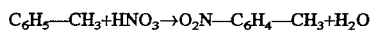

$$C_6H_5\text{—}CH_3 + HNO_3 \rightarrow O_2N\text{—}C_6H_4\text{—}CH_3 + H_2O$$

Thus toluene and $HNO_3$ are introduced into the process and mononitrotoluene and $H_2O$ are ejected, while the $H_2SO_4/H_2O$ mixture described represents the reaction medium. Since, when the process is carried out industrially, dilute nitric acids are advantageously used, depending on the price of the nitric acids respectively available, additionally to the reaction water, dilution $H_2O$ of the $HNO_3$ must also be ejected.

The organic phase arising in the separation of the reaction mixture can be worked up to give pure mononitrotoluene or be fed to the dinitrotoluene preparation. In the former case at least molar amounts of toluene or a slight molar excess will be used, as described above, in order not only to consume the $HNO_3$ but also to repress the second nitration; any toluene excess is distilled off from the organic phase separated off. Before this, the organic phase can be washed in order to separate off water-, acid- or alkali-soluble impurities, such as inorganic and organic salts and phenolic impurities. However, the formation of oxidation products (phenols, oxidation of the $CH_3$ group) is strongly suppressed in the process according to the invention. Likewise, the formation of dinitrotoluenes is highly repressed. However, these dinitrotoluenes are not an interference if a second nitration is in any case intended; therefore, in such cases, the procedure may also be carried out with a toluene excess.

As a model for a continuously-operated back mixing-free industrial reactor, an to represent the discontinuous procedure, a batch formulation in a vigorously stirred, heat-insulated stirred flask, e.g. in a so-called sulphitation beaker, which is furnished with baffles, conserve in the laboratory. In this case toluene, sulphuric acid and water are introduced, e.g. at 85° C., and nitric acid, which is heated to the feed temperature according to the invention and which can be diluted by water and/or sulphuric acid, is added in approximately 1 to 2 seconds. As an alternative to the dosing variants described, the total amount of nitric acid, sulphuric acid and water can, for example, be introduced at the feed temperature according to the invention and the toluene heated to the feed temperature according to the invention can be added in approximately 1 to 2 seconds. After the addition, the reaction is allowed to proceed adiabatically in both cases with vigorous stirring. Still further dosing variants are easily recognizable to those skilled in the art. The final temperature, equivalent to the end of the reaction, is achieved within at most 300 seconds, depending on the energy input via the stirrer and depending on concentration of the $H_2SO_4$. The contents of the reaction vessel correspond in this case in the course of time to a part-volume in the axial movement through a tubular reactor with plug flow. That which occurs successively in time in the batch formulation proceeds successively with respect to position in, for example, a tubular reactor.

In this laboratory embodiment of the process according to the invention, after the work-up, within the limits of the analytical variation, mononitrotoluenes having, for example, the following isomeric distribution are obtained:

| 2-nitrotoluene: | approximately 58–60% |
|---|---|
| 3-nitrotoluene: | approximately 4–6% |
| 4-nitrotoluene: | approximately 35–37% |

The yield of mononitrotoluenes, based on nitric acid used, is >95% of the theoretical yield in this case, frequently >97%; in the continuous procedure, it reaches values >98%.

If a reaction mixture having a relatively low content of 3-nitrotoluene is desired, the reaction participants are preferably mixed in the lower temperature range of about 20° to 80° C. and, if required, additional $HNO_3$ added at relatively low concentrations of 1 to 2.5% by weight is employed. In this case, the substantially $HNO_3$-free waste acid likewise arises at lower temperature, so that flash concentration is carried out at lower pressures, e.g. at 1–70 mbar.

After the final reaction temperature has been achieved, the stirrer is halted. The phases separate in approximately 20 seconds. A continuous industrial reactor is preferably dimensioned in such a way that the reaction mixture reaches the final reaction temperature in the reactor.

The acid phase separated off after the reaction at the level of the respective final reaction temperature is light-yellow to light-brown and is concentrated in the manner described above, the reactive extraction described above being able to be inserted. The circulated $H_2SO_4$ thus conducted then contains less than 25 ppm of nitric acid and less than 25 ppm of nitrous acid, e.g. 5 to 20 ppm each, and small amounts of organic carbon-containing impurities.

If the reaction procedure according to the invention is departed from, e.g. in such a manner that, for example, when the procedure is carried out on a laboratory scale, toluene, sulphuric acid and water are introduced into a heat-insulated stirred flask (sulphitation beaker) at the feed temperature according to the invention and nitric acid, which is diluted by water and sulphuric acid, is added slowly, e.g. in 30 minutes, in this case departing from the intensive and rapid mixing of the total amount of all reaction participants and thus permitting a substantially complete, but undesirable according to the invention, back-mixing, a black reaction mixture is obtained (Example 3). The tarry organic phase still contains approximately 40 to 50% of unreacted toluene in its volatile portions. Since corresponding experiments carried out in a reaction calorimeter showed that these reaction conditions proceed with about double the reaction enthalpy in comparison with the procedure according to the invention and is associated with an intensive development of gas, further investigations and clarifications in this direction were dispensed with.

EXAMPLE 1

653.8 g of sulphuric acid and 297.9 g of water were introduced at 85° C. into a heat-insulated sulphitation beaker (diameter 100 mm), furnished with baffles and 2 turbine stirrers (diameter 39.9 mm) seated on a shaft and the mixture was stirred at 1800 rpm. The specific stirrer power introduced as a result was 22 W/l. 50.7 g (0.55 mol) of toluene were then added in 1 to 2 seconds and, immediately afterward, a mixture, heated to 85° C., of 31.5 g (0.5 mol) of nitric acid, 34.4 g of sulphuric acid and 32.6 g of water were added, likewise in 1 to 2 seconds, and the mixture was reacted without cooling. After 105 seconds, the final temperature of 110.5° C. was achieved and the stirrer was halted. The phase separation was complete after 15 seconds. 71.7 g of organic phase of the following composition (calibrated GC) were isolated:

| toluene: | 6.00 |
|---|---|
| 2-nitrotoluene: | 54.20% (relative 58.3%) |
| 3-nitrotoluene: | 5.60% (relative 6.02%) |
| 4-nitrotoluene: | 33.20% (relative 35.7%) |
| 2,4-dinitrotoluene: | 0.14% |
| 2,6-dinitrotoluene: | 0.05% |
| dinitro-p-cresol: | 0.60% |
| dinitro-o-cresol: | 0.17% |
| unknown: | remainder |

This corresponds to a yield of mononitrotoluenes of 97.2% of the theoretical yield. The portions of up to 2% contained in the inorganic phase are accessible by extraction or distillation.

EXAMPLE 2

688.5 g of sulphuric acid, 330.2 g of water and 31.5 g (0.5 mol) of nitric acid were introduced at 85° C. as in Example 1 into a heat-insulated sulphitation beaker and the mixture was stirred at 1200 rpm. The specific stirrer power introduced as a result was 8.7 W/l. 55.3 g (0.6 mol) of toluene heated to 85° C. were added in 1 to 2 seconds and the mixture was allowed to react without cooling. After 110 seconds, the final temperature of 110.5° C. was reached and the stirrer was halted. The phase separation was complete after 20 seconds. 73.8 g of organic phase of the following composition (calibrated GC) were isolated:

| toluene: | 10.50% |
|---|---|
| 2-nitrotoluene: | 51.40% (relative 58.1%) |
| 3-nitrotoluene: | 5.40% (relative 6.10%) |
| 4-nitrotoluene: | 31.70% (relative 35.8%) |
| 2,4-dinitrotoluene: | 0.13% |
| 2,6-dinitrotoluene: | 0.05% |
| dinitro-p-cresol: | 0.51% |
| dinitro-o-cresol: | 0.18% |
| unknown: | remainder |

This corresponds to a yield of mononitrotoluenes in the organic phase of 95.2% of the theoretical yield.

EXAMPLE 3

(for comparison)

653.8 g of sulphuric acid, 297.9 g of water and 50.7 g (0.55 mol) of toluene were introduced at 85° C., as in Example 1, into a heat-insulated sulphitation beaker and the mixture was stirred at 1800 rpm (22 W/l specific stirrer power). A mixture of 31.5 g (0.5 mol) of nitric acid, 34.4 g of sulphuric acid and 32.6 g of water, heated to 85° C., was added in the course of 30 minutes and the mixture was allowed to react without cooling. The temperature increased in this case to 100.5° C. (heat losses due to the long reaction time) and the total reaction mixture turned black with foaming. After phase separation (more than 16 hours), 53.0 g of black organic phase was isolated, the volatile portions of which had the following composition:

| | |
|---|---|
| toluene: | 41.9% |
| 2-nitrotoluene: | 31.1% |
| 3-nitrotoluene: | 3.1% |
| 4-nitrotoluene: | 18.6% |
| unknown: | remainder |

EXAMPLE 4

(for comparison)

133.6 g of sulphuric acid and 55.9 g of water were introduced at 85° C., as in Example 1, into a heat-insulated sulphitation beaker and the mixture was stirred at 1800 rpm (22 W/l specific stirrer power). 50.7 g (0.55 mol) of toluene were then added in the course of approximately 1 to 2 seconds and, immediately thereafter, a mixture of 31.5 g (0.5 mol) of nitric acid, 47.7 g of sulphuric acid and 19.3 g of water, heated to 85° C., was added, likewise in the course of 1 to 2 seconds, and the mixture was allowed to react without cooling. After 20 seconds, the final temperature of 120° C. was reached and the stirrer was halted. The homogeneous brown solution was drained off onto approximately 1 kg of ice and the solid separated off during this were filtered off using suction. The moist solids (48.4 g) contained, according to HPLC, 32.1% by weight of 4-nitrotoluene-2-sulphonic acid (remainder: water and sulphuric acid).

From the mother liquor, 1.9 g of organic compounds of the composition below were isolated by extraction with methylene chloride:

| | |
|---|---|
| 2-nitrotoluene: | 3.7% |
| 3-nitrotoluene: | 0.4% |
| 4-nitrotoluene: | 0.1% |
| 2,4-dinitrotoluene: | 78.2% |
| 2,6-dinitrotoluene: | 6.1% |
| unknown: | remainder |

The aqueous phase (2250 g) extracted contained, according to HPLC, 3.3% by weight of 2-nitrotoluene-4-sulphonic acid.

EXAMPLE 5

662.2 g of sulphuric acid, 313.8 g of water and 25.3 g (0.275 mol) of toluene were introduced at 50° C., as in Example 1, into a heat-insulated sulphitation beaker and the mixture was stirred at 1800 rpm (22 W/l specific stirrer power). A mixture of 15.8 g (0.25 mol) of nitric acid, 33.9 g of sulphuric acid and 24.6 g of water, heated to 50° C., was added in the course of 1–2 seconds and the mixture was allowed to react without cooling. After 220 seconds, the final temperature of 64° C. was reached and the stirrer was halted. The phase separation was complete after 90 seconds. 35.5 g of organic phase of the composition below (calibrated GC) were isolated:

| | |
|---|---|
| toluene: | 6.2% |
| 2-nitrotoluene: | 55.3% |
| 3-nitrotoluene: | 4.61% |
| 4-nitrotoluene: | 31.9% |
| 2,4-dinitrotoluene: | 0.01% |
| 2,6-dinitrotoluene: | 0.0% |
| dinitro-p-cresol: | 0.86% |
| dinitro-o-cresol: | 0.22% |
| unknown: | remainder |

This corresponds to a yield of mononitrotoluenes of 95.0% of the theoretical yield.

EXAMPLE 6

662.2 g of sulphuric acid, 313.8 g of water and 25.3 g (0.275 mol) of toluene were introduced at 70° C., as in Example 1, into a heat-insulated sulphitation beaker and the mixture was stirred for 1800 rpm (22 W/l specific stirring power). A mixture of 15.8 g (0.25 mol) of nitric acid, 33.9 g of sulphuric acid and 24.6 g of water, heated to 70° C., was added in the course of 1–2 seconds and the mixture was allowed to react without cooling. After 180 seconds, the final temperature of 84° C. was reached and the stirrer was halted. The phase separation was complete after 50 seconds. 35.6 g of organic phase of the composition below (calibrated GC) were isolated:

| | |
|---|---|
| toluene: | 6.3% |
| 2-nitrotoluene: | 54.4% |
| 3-nitrotoluene: | 5.05% |
| 4-nitrotoluene: | 32.6% |
| 2,4-dinitrotoluene: | 0.02% |
| 2,6-dinitrotoluene: | 0.01% |
| dinitro-p-cresol: | 0.71% |
| dinitro-o-cresol: | 0.22% |
| unknown: | remainder |

This corresponds to a yield of mononitrotoluenes of 95.6% of the theoretical yield.

EXAMPLE 7

339.2 g of sulphuric acid, 128.9 g of water and 33.7 g (0.366 mol) of toluene were introduced at 50° C., as in Example 1, into a heat-insulated sulphitation beaker and the mixture was stirred at 1800 rpm (22 W/l specific stirring power). A mixture, heated to 50° C., of 21.0 g (0.333 mol) of nitric acid, 17.9 g of sulphuric acid and 6.8 g of water was added in the course of 1–2 seconds and the mixture was allowed to react without cooling. After 165 seconds, the final temperature of 85° C. was reached and the stirrer was halted. The phase separation was complete after 50 seconds. 47.5 g of organic phase of the composition below (calibrated GC) were isolated:

| | |
|---|---|
| toluene: | 6.2% |
| 2-nitrotoluene: | 54.6% |
| 3-nitrotoluene: | 4.7% |
| 4-nitrotoluene: | 33.6% |
| 2,4-dinitrotoluene: | 0.11% |
| 2,6-dinitrotoluene: | 0.06% |
| dinitro-p-cresol: | 0.49% |
| dinitro-o-cresol: | 0.07% |
| unknown: | remainder |

This corresponds to a yield of mononitrotoluenes of 96.7% of the theoretical yield.

EXAMPLE 8

653.8 g of sulphuric acid, 297.9 g of water and 50.7 g (0.55 mol) of toluene were introduced at 50° C., as in Example 1, into a heat-insulated sulphitation beaker and stirred at 1800 rpm (22 W/l specific stirring power). A mixture, heated to 50° C., of 31.5 g (0.5 mol) of nitric acid, 34.4 g of sulphuric acid and 32.6 g of water was added in the course of 1-2 seconds and the mixture was allowed to react without cooling. After 203 seconds, the final temperature of 75° C. was reached and the stirrer was halted. The phase separation was complete after 45 seconds. 72.4 g of organic phase of the composition below (calibrated GC) were isolated:

| | |
|---|---|
| toluene: | 6.50% |
| 2-nitrotoluene: | 55.10% |
| 3-nitrotoluene: | 4.70% |
| 4-nitrotoluene: | 32.1% |
| 2,4-dinitrotoluene: | 0.02% |
| 2,6-dinitrotoluene: | 0.01% |
| dinitro-p-cresol: | 0.69% |
| dinitro-o-cresol: | 0.16% |
| unknown: | remainder |

This corresponds to a yield of mononitrotoluenes of 97.0% of the theoretical yield.

EXAMPLE 9

450.8 g of sulphuric acid, 158.9 g of water and 46.1 g (0.5 mol) of toluene were introduced at 25° C., as in Example 1, into a heat-insulated sulphitation beaker and stirred at 1200 rpm (8.7 W/l specific stirring power). A mixture, heated to 25° C., of 21.0 g (0.333 mol) of nitric acid, 23.7 g of sulphuric acid and 19.7 g of water was added in the course of 1-2 seconds and the mixture was allowed to react without cooling. After 315 seconds, the final temperature of 52° C. was reached and the stirrer was halted. The phase separation was complete after 75 seconds. 60.4 g of organic phase of the composition below (calibrated GC) were isolated:

| | |
|---|---|
| toluene: | 25.60% |
| 2-nitrotoluene: | 42.86% |
| 3-nitrotoluene: | 3.14% |
| 4-nitrotoluene: | 26.41% |
| 2,4-dinitrotoluene: | 0.02% |
| 2,6-dinitrotoluene: | 0.01% |
| dinitro-p-cresol: | 0.31% |
| dinitro-o-cresol: | 0.08% |
| unknown: | remainder |

This corresponds to a yield of mononitrotoluenes of 95.8% of the theoretical yield.

We claim:

1. A process for the continuous preparation of mononitrotoluenes by reaction of toluene with an $HNO_3/H_2SO_4/H_2O$ mixture with formation, essentially, of mononitrotoluenes and reaction water, comprising the steps of
   a) feeding the reaction participants toluene, $HNO_3$, $H_2SO_4$ and $H_2O$ into a continuous tubular reactor equipped with static mixer elements, in which
      a1) the amount of $HNO_3$ is 1–8% by weight, the amount of $H_2SO_4$ is 58–74% by weight and the amount of $H_2O$ is the remainder to 100% by weight and 100% by weight signifies the sum of $HNO_3+H_2SO_4+H_2O$,
      a2) the $H_2O$ is used as such, as dilution $H_2O$ of the $HNO_3$, as dilution of the $H_2SO_4$ or in a plurality of the said forms, and
      a3) the molar ratio of toluene to $HNO_3$ is 0.9–1.5,
   b) rapidly and intensively mixing the totality of the reaction participants employing a mixing energy of 3 to 40 watts per liter of the total reaction mixture, with at least two redispersions of the total reaction mixture,
   c) carrying out the reaction under adiabatic conditions, the reaction participants being fed in at temperatures such that the mixing proceeds in the range of 20°–110° C., and the temperature at the end of the reaction does not exceed 135° C.,
   d) separating the reaction mixture, after carrying out the reaction, into an organic and an inorganic phase and
   e) working-up the substantially $HNO_3$-free inorganic phase by distillation with removal of water.

2. The process of claim 1, wherein the mixing energy employed in step b) is 3 to 30 W/l of the total reaction mixture.

3. The process of claim 1, wherein the mixing in step c) proceeds in the range of 30°–100° C.

4. The process of claim 3, wherein the mixing in step c) proceeds in the range of 40° to 90° C.

5. The process of claim 1, which is carried out continuously and for this a tubular reactor is used which substantially prevent the back-mixing of the reaction participants.

6. The process of claim 5, wherein the reaction participants, before entry into the reactor substantially preventing back-mixing, are intensively mixed with the aid of mixing elements within a time of less than 3 sec. and, on flowing through the reactor, are redispersed at least twice.

7. The process of claim 1, wherein in step e), the heat of reaction absorbed by the inorganic phase, as a result of the adiabatic reaction conditions, is utilized for the ejection by distillation of water at a pressure of 1–100 mbar.

8. The process of claim 7, wherein the distillation of water is carried out at a pressure of 5–80 mbar.

9. The process of claim 7, wherein by the distillation of water, $H_2SO_4$ is produced which is recycled to step a).

10. The process of claim 1, wherein the sulphuric acid content in the inorganic phase according to step d) is 62 to 74% by weight.

11. The process of claim 10, wherein the sulfuric acid content in the inorganic phase according to step d) is 64 to 72% by weight.

12. The process of claim 1, wherein the content of added nitric acid in the reaction mixture at the time of mixing, based on the sum of nitric acid, sulphuric acid and water, is 1 to 6% by weight.

13. The process of claim 12, wherein the content of added nitric acid is 1.5 to 4% by weight.

14. The process of claim 1, wherein the content of sulphuric acid in the reaction mixture at the time of mixing, based on the sum of nitric acid, sulphuric acid and water, is 60–72% by weight.

15. The process of claim 14, wherein the content of sulfuric acid is 61–69% by weight.

16. The process of claim 1, wherein the molar ratio of toluene to nitric acid is greater than 1.0 up to 1.5.

17. The process of claim 16, wherein the molar ratio of toluene to nitric acid is 1.03 to 1.3.

18. The process of claim 1, wherein in the work-up by distillation in step e), the $H_2SO_4$ is concentrated by 0.6 to 7 percentage points.

19. The process of claim 18, wherein the $H_2SO_4$ is concentrated by 1.5 to 3 percentage points.

20. The process of claim 5, wherein the $H_2SO_4$ is recovered for reuse by removing water by distillation.

* * * * *